United States Patent [19]
Erb et al.

[11] Patent Number: 5,952,035
[45] Date of Patent: Sep. 14, 1999

[54] SURFACE TREATMENT AND LIGHT INJECTION METHOD AND APPARATUS

[75] Inventors: Judith Erb; James Downward, IV, both of Ann Arbor, Mich.

[73] Assignee: IA, Inc., Ann Arbor, Mich.

[21] Appl. No.: 08/864,244

[22] Filed: May 28, 1997

Related U.S. Application Data

[62] Division of application No. 08/616,576, Mar. 15, 1996, Pat. No. 5,854,863.

[51] Int. Cl.$^6$ ....................................................... B05D 3/00
[52] U.S. Cl. ...................... 427/2.11; 427/163.2; 427/271; 427/336
[58] Field of Search ............................... 427/163.2, 385.5, 427/389.7, 271, 2.11, 336, 384

[56] References Cited

U.S. PATENT DOCUMENTS

| | | |
|---|---|---|
| 3,604,927 | 9/1971 | Hirschfeld . |
| 3,939,350 | 2/1976 | Kronick et al. . |
| 3,975,084 | 8/1976 | Block . |
| 3,998,591 | 12/1976 | Eckefeldt . |
| 4,018,530 | 4/1977 | Hirschfeld . |
| 4,050,895 | 9/1977 | Hardy et al. . |
| 4,100,416 | 7/1978 | Hirschfeld . |
| 4,106,909 | 8/1978 | David et al. . |
| 4,133,639 | 1/1979 | Harte . |
| 4,321,057 | 3/1982 | Buckles . |
| 4,367,918 | 1/1983 | Pinnow ................................ 427/163.2 |
| 4,368,047 | 1/1983 | Andrade et al. . |
| 4,447,546 | 5/1984 | Hirschfeld . |
| 4,530,569 | 7/1985 | Squire . |
| 4,558,014 | 12/1985 | Hirschfield et al. . |
| 4,560,248 | 12/1985 | Cramp et al. . |
| 4,564,532 | 1/1986 | Henderson . |
| 4,582,802 | 4/1986 | Zimmerman et al. . |
| 4,582,809 | 4/1986 | Block . |
| 4,608,344 | 8/1986 | Carter . |
| 4,654,532 | 3/1987 | Hirschfeld . |
| 4,716,121 | 12/1987 | Block . |
| 4,775,637 | 10/1988 | Sutherland et al. . |
| 4,787,709 | 11/1988 | Kawadi et al. ....................... 427/163.2 |
| 4,800,279 | 1/1989 | Hieftje et al. . |
| 4,810,658 | 3/1989 | Shanks et al. . |
| 4,818,710 | 4/1989 | Sutherland et al. . |
| 4,836,642 | 6/1989 | Matsumoto et al. ................. 427/163.2 |
| 4,844,869 | 7/1989 | Glass . |
| 4,857,273 | 8/1989 | Stewart . |
| 4,877,747 | 10/1989 | Stewart . |
| 4,880,752 | 11/1989 | Keck et al. . |
| 4,889,407 | 12/1989 | Markle et al. . |
| 4,909,990 | 3/1990 | Block . |
| 4,985,308 | 1/1991 | Squire et al. ........................ 427/163.2 |
| 4,992,385 | 2/1991 | Godfrey . |
| 5,037,615 | 8/1991 | Kane . |
| 5,045,282 | 9/1991 | Kritzman et al. . |
| 5,076,659 | 12/1991 | Bekiarian et al. . |
| 5,082,629 | 1/1992 | Burgess, Jr. et al. . |
| 5,094,819 | 3/1992 | Yager et al. . |
| 5,102,526 | 4/1992 | Brown et al. . |
| 5,109,442 | 4/1992 | Klainer et al. ...................... 427/163.2 |
| 5,130,265 | 7/1992 | Battiloti et al. . |
| 5,135,876 | 8/1992 | Andrade et al. . |
| 5,156,976 | 10/1992 | Slovacek et al. . |
| 5,192,510 | 3/1993 | Zoha et al. . |
| 5,194,393 | 3/1993 | Hugl et al. . |
| 5,221,958 | 6/1993 | Bohnenkamp . |
| 5,240,586 | 8/1993 | Moore et al. . |
| 5,242,837 | 9/1993 | Slovaoek et al. . |
| 5,271,073 | 12/1993 | Hui et al. ............................. 427/163.2 |

FOREIGN PATENT DOCUMENTS

| | | |
|---|---|---|
| 0 075 353 A1 | 9/1982 | European Pat. Off. . |
| 0 239 382 A2 | 3/1987 | European Pat. Off. . |
| 3 605 518 | 8/1987 | Germany . |

OTHER PUBLICATIONS

Du Pont Polymers, Teflon AF, Product Information, (Adhesion Information for Teflon AF), Oct. 1992, 2 pages, Printed in U.S.A.

Product Environmental Data 3M, Specialty Chemicals Division Fluorinert Brand Electronic Liquid FC–75, Mar. 15, 1993, 3 pages, U.S.A.

*Primary Examiner*—Janyce Bell
*Attorney, Agent, or Firm*—Kohn & Associates

[57] ABSTRACT

A biological sensor 10 having a beam/light shaper 30 which is adapted to inject light into the sensor at substantially the critical angle with respect to the side surface of the sensor. The sensor 10, of the preferred embodiment of the invention, further may undergo a surface treatment which reduces/eliminates non-specific binding to the sensor surface and a treatment process to reduce light energy losses occurring by mounting and/or inserting the fiber portion of the sensor into the medium of interest. Both the light injection and surface treatment methodologies have utility apart from the biological immunoassay sensor embodiment described and claimed in this Application and may be independently applied to a biological sensor.

2 Claims, 3 Drawing Sheets

SURFACE TREATMENT AND LIGHT INJECTION METHOD AND APPARATUS

This is a divisional of application Ser. No. 08/616,576 filed on a Mar. 15, 1996 now U.S. Pat. No. 5,854,863.

FIELD OF THE INVENTION

This invention generally relates to a surface treatment method and to an apparatus made and/or treated in accordance with the method, and more particularly, in one embodiment, to a method to treat the surface of a biological sensor, such as a fiber optic biological sensor, in order to reduce and/or eliminate the binding of certain constituents to the sensor surface when the binding occurs by mechanisms other than the affinity binding between a biological recognition molecule and its binding partner, and to a biological sensor made and/or treated in accordance with the surface treatment methodology of the invention. This invention also relates to a method and to an apparatus made in accordance with the method for injecting light energy into a biological sensor which provides an evanescent field of greater efficiency, uniformity, and strength than previously produced. This evanescent field methodology may selectively be used in combination with the surface treatment methodology to provide a biological sensor which is greatly improved over the prior art. Alternatively, the surface treatment and light injection methodologies of the invention may be singularly used to provide a biological sensor greatly improved over the prior art in a singular area. Moreover, the surface treatment methodologies of the present invention may be singularly and independently used in virtually any context where it is desirable to protect a generally solid surface, such as of the glass or silicon, type, from non-specific binding by proteins. This invention also relates to a fiber surface treatment methodology to eliminate and/or reduce light energy losses caused by mounting the fiber into the test medium.

BACKGROUND OF THE INVENTION

Biological sensors, and more particularly, fiber optic biological sensors are generally used to determine the presence, absence, and/or concentration of certain chemical and/or molecular constituents occurring in a medium. In practice, a fiber optic type biological sensor is normally used in such applications. That is, in practice, the biological sensor utilizes an optical fiber, having at least a first portion which is immersed into the medium and a second portion which receives light energy. More particularly, the first portion generally receives injected light energy and communicates the received light energy to the fiber portion which is resident or immersed within the medium.

A first chemical and/or molecular constituent which is known to form an affinity complex with the second constituent occurring in the medium is generally and normally directly and/or indirectly attached to the surface of at least the immersed portion of the fiber. The second constituent occurring in the medium is selectively tagged with fluorescent molecules or other molecules which either generate light energy in the presence of an evanescent energy field, or absorb energy from an evanescent field thereby altering the transmission of light through the fiber. As the fiber is immersed into the medium, some amount of the second constituent typically binds with the first constituent.

As light is received into the first portion of the fiber and communicated to the medium immersed fiber portion, an evanescent field is created around the immediate vicinity of the surface of the fiber. This evanescent field causes fluorescent tags occurring in very close proximity to the fiber surface (e.g. only those tags attached to the portions of the second constituent which become actually bound to the fiber surface) to radiate light energy, at some known and predetermined wavelength dependent upon the type and identity of employed tag. This radiated light energy is "tunneled" or communicated into the fiber and subsequently propagated and communicated to a receiver or detector. The amount of such received tunneled light is known to be directly proportional to the amount of the second constituent which binds to the fiber surface. This binding of this second constituent varies either directly or inversely, depending upon experimental design, with the amount or concentration of the second constituent occurring in the medium. In this manner, based upon the intensity of the received evanescently produced light, a calculation is made of the absence, presence, and/or concentration of the second constituent which is occurring in the medium. As previously mentioned other types of energy absorbing molecules may be used to alter the transmission of the tunneled light within the fiber. These absorbing molecules replace the fluorescent tags and represent a different invention embodiment. The concentration or amount of such absorbing molecules in close proximity to the sensor surface (e.g. attached to the second constituent adhering or binding to the first constituent) changes the amount of tunneled light received from the fiber and such change is directly or inversely proportional to the concentration of the second constituent occurring in the medium.

While these biological sensors are generally effective in determining the presence of the second constituent in the medium they suffer from many drawbacks, especially when used to determine the exact medium concentration of the second constituent.

Because such sensors rely upon the specific binding between the fluorescent-tagged constituent and its binding partner at the fiber surface, binding of the fluorescent-tagged constituent to the surface of the fiber in a manner which does not rely upon the specific affinity binding to the binding partner creates a false signal. More particularly, such binding results in fluorescence which is tunneled and communicated to the receiver, but which does not reflect any quantitative relationship between the recognition molecule and its binding partner. This diminishes the accuracy of the sensor. Such binding of molecules to the fiber surface in a manner which does not rely upon specific affinity binding between a recognition molecule (e.g. first constituent) and its partner (e.g. second constituent) is designated as "non-specific binding". In the case of immunobinding, the antibody is the recognition molecule and the antigen is the partner.

The non-specific binding of non-fluorescent constituents in a biological sample to the surface of the fiber can also adversely affect sensor operation by obscuring the binding partner on the fiber surface thereby interfering with the specific binding between the recognition protein and its ligand on the fiber surface. There is therefore a great need to provide a methodology to reduce and/or eliminate such "nonspecific" binding upon the biological sensor, and there is a further need to provide and to construct a biological sensor upon which constituents do not bind nonspecifically. Such non-specific binding similarly and detrimentally affects binding methodologies using energy absorption molecules in place of the fluorescent tags.

Yet another drawback to these prior biological sensors is that the evanescent field created by injecting light using conventional optical methods is not uniformly generated along the fiber surface and/or is relatively weak in some parts of the sensor surface. This lack of uniformity and weakness prevents some of the bound and tagged constituents from being "counted" or induced to fluoresce, or from absorbing and hence "changing" the evanescent field. Hence, the resulting concentration calculation is incorrect. There is therefore also a need to provide a methodology to increase the strength and/or efficiency of the generated evanescent field and to ensure that the field is substantially and uniformly generated about the fiber. There is also a great need for a biological sensor employing this evanescent field enhancement methodology.

Yet another drawback to these prior optical fiber biological sensors is that the majority of injected light rays traveling within the fiber sensor couple only weakly to the evanescent field at the fiber surface because they do not all impinge on the inside fiber surface at angles (as measured between the fiber surface and the light ray) near to but not greater than the critical angle for the fiber-liquid interface. As a result, the coupling of injected light via the evanescent field to bound and tagged constituents on the fiber surface is less than optimal, the fluorescence stimulated by this evanescent field is reduced, and ultimately the fluorescence from the tagged constituent which is coupled back through the fiber sensor to a fluorescence measuring device is significantly reduced. While techniques such as chemically etching a taper into fiber sensors have been used to concentrate more of the injected light rays into angles close to the critical angle, such techniques have led to fiber sensors which are hard to manufacture, large in size, and which concentrate the injected light only within a section of the fiber sensor.

Yet a further drawback associated with these prior optical fiber biological sensors is that a relatively large amount of the light radiation which is input and output from the sensor is lost due to the nature of the sensor supporting structure and/or to the method by which the fiber optic structure is supported or "held" into the medium of interest.

There is therefore a need to provide a methodology to increase the strength and/or efficiency of the coupling of the injected light to the evanescent field and to insure that the field is substantially and uniformly generated about the sensitized region of the fiber sensor so that small and highly sensitive fiber sensors can be easily manufactured. There is also a great need for a biological sensor employing this evanescent field enhancement methodology. There is also a need to provide a biological fiber optic sensor and sensor support assembly and/or fiber optic structural support methodology which reduces light energy loss associated with the prior art sensor assemblies.

SUMMARY OF THE INVENTION

It is a first general object of this invention to provide a biological sensor which overcomes and/or eliminates the previously delineated drawbacks of the various biological immunoassay sensors of the prior art.

It is a second general object of this invention to provide a methodology to reduce and/or eliminate the binding of "undesirable" constituents and/or "non-specific" constituents to a generally solid surface which may be of the glass or silicon type, including but not limited to the surface of an optical fiber employed within a biological sensor.

It is a third general object of this invention to provide a biological sensor, made in accordance with the teachings of the preferred surface treatment methodology of this invention. The sensor, includes a surface which is treated by the surface treatment methodology of the invention and which provides increased computation accuracy of the presence, absence, and/or concentration of a constituent of interest which is present in a certain medium.

It is a fourth general object of the invention to provide a methodology to generate an evanescent field about the surface of an optical fiber with greater efficiency and strength than previously realized by prior methodologies.

It is a fifth general object of the invention to provide a methodology to generate an evanescent field about the surface of an optical fiber of greater efficiency, strength, and/or uniformity than previously realized by prior methodologies.

It is a sixth general object of the invention to provide a biological sensor assembly made in accordance with the teachings of the preferred light injection and/or light shaping methodology of this invention. More particularly, the biological sensor includes an optical fiber for receiving light; and light injecting means for causing the received light to be of a certain predetermined form sufficient to ensure that the light, received by the optical fiber, forms an angle with respect to the side surface of the fiber which is substantially equal to the critical angle.

It is a seventh general object of the invention to provide a biological immunoassay sensor assembly having an optical fiber whose surface is treated by the treatment methodology of the invention; a light energy generator for generating light; and a light shaper for ensuring that the generated light is communicated to the fiber at an angle substantially equal to the critical angle with respect to the side surface of the fiber.

It is a eighth general object of the invention to provide a biological immunoassay sensor having improved light energy loss characteristics over that of the prior art.

It is a ninth general object of the invention to provide a biological immunoassay sensor having an improved sensor supporting and/or medium placement methodology which reduces the amount of light energy loss over that associated with the prior art.

According to the teachings of a first embodiment of this invention, a method to treat a glass or silicon surface effective to substantially reduce or eliminate the binding of "undesirable" and/or "non-specific" constituents to the surface is provided. The method comprises the steps of applying a chemical from the group consisting of amorphous fluoro-polymers to the surface; baking the surface for a predetermined period of time at a predetermined temperature; and removing all or part of the applied chemical from the surface by, in one embodiment, exposing that surface to a chemical which dissolves some or all of the applied chemical.

According the teachings of a second embodiment of this invention, a biological sensor is provided. The sensor includes an optical fiber having a surface which is prepared in accordance with the surface treatment methodology set forth in the first embodiment of the invention, and further being adapted to operate with a light source which generates and injects light energy into the treated optical fiber and a receiver which is in optical communication with the optical fiber and which receives light generated by an interaction of an evanescent field produced by the generated and injected light energy and certain constituents which are bound to the surface of the fiber.

According to the teachings of a third embodiment of the invention, a methodology to hold an optical fiber into a medium is provided. The methodology includes the steps of placing a coating substance from the family of substances having a refractive index which is approximately equal to or lower than that of the medium surrounding the active region of the fiber, at each opposed end of the optical fiber; and attaching the treated optical fiber, at only the treated ends, in a sample cell. In one embodiment, this substance comprises Teflon-AF®.

These and other objects, features, and advantages of the present invention will become apparent from the foregoing discussion in combination with the attached drawings, subjoined claims, and detailed description of the preferred embodiment of the invention. Moreover, it should be realized by one of ordinary skill in the art that the non-specific binding surface treatment methodology, light injection methodology, and surface treatment and fiber placement methodologies of the invention are mutually exclusive and that all, two, or any one of the methodologies may be selectively and independently used to create a biological immunoassay sensor.

BRIEF DESCRIPTION OF THE DRAWINGS

For a fuller and more complete understanding of the nature and objects of the present inventions, reference should be had to the following drawings in which.

DETAILED DESCRIPTION OF THE PREFERRED EMBODIMENT OF THE INVENTION

Figure 1:
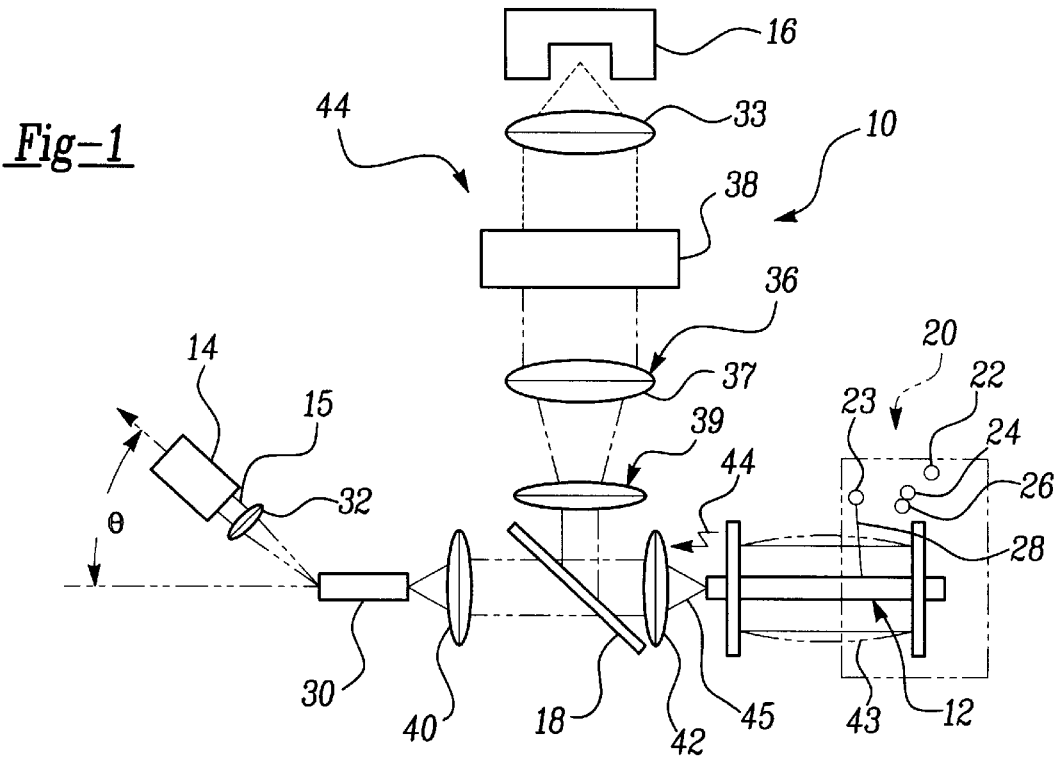
FIG. 1 is a schematic view of an exemplary immunochemical biological sensor embodying the principles of the present invention and used in the various experiments detailed in this application and further showing an exploded view of medium 20 which, in the preferred embodiment of the invention, is constrained to be within a relatively short distance, such as 0.55 mm, around the fiber.

Referring now to FIG. 1 there is shown a biological immunoassay/immunochemical sensor assembly 10 made in accordance with the teachings of one embodiment of the invention and employing one embodiment of the light injecting methodology and the surface treatment methodology of the invention. For purposes of the following discussion, the term "sensor" refers only to optical fiber 12 while the term "sensor assembly" includes all of the elements shown in FIG. 1. Moreover, it should be understood by those of ordinary skill in the art that while the following description refers to a biological sensor of the fiber optic type; other types of biological sensors may utilize the various methodologies of the invention and form biological sensor assemblies coming within the scope of the subjoined claims. Moreover, it should further be apparent that the various light injection and surface treatment methodologies may have utility in combination with other types of non-biological sensor apparatuses.

More particularly, biological sensor assembly 10 includes an optical fiber 12 which is treated by the surface treatment methodology of the preferred embodiment of the invention, a light source 14, comprising, in one embodiment, a commercially available laser which generates light energy at a wavelength of about 633 nano-meters, a photodetector or light energy detector 16 which comprises, in one embodiment, a photodiode manufactured by the EG & G Company and referred to as model FND100, and a beamsplitter 18 which comprises, in one embodiment, a commercially available splitter referred to as a "50/50" type and having a diameter of about ¼". Light source 14, photodetector 16, and beamsplitter 18, of the preferred embodiment of the invention respectively and generally correspond to light source 20, photodetector 26, and beamsplitter 22 shown and described in U.S. Pat. No. 4,582,809 ("the '809 patent") which was filed on Aug. 9, 1982, given application Ser. No. 406,324, which is a continuation-in-part of application Ser. No. 388,193, which was filed on Jun. 14, 1982, and which is fully and completely incorporated into this Application by reference, word for word and paragraph by paragraph. That is, all of the material disclosed and claimed in the '809 Patent is fully and completely incorporated into this present Application by reference.

As further shown in FIG. 1, at least a portion of fiber 12 is further adapted to be placed into medium 20 containing a component 22 of a complex forming one part of an immunochemical reaction and whose presence, absence, and/or concentration is desired to be calculated and/or measured. Molecules 23 of a type capable of competing with component 29 for the formation of a complex with a second component 26, are attached to optical fiber 12 by means of a silane molecular chain 28. Component 26 is coupled to or compounded with a fluorophore tag 24. One method for preparing the surface of fiber 12 and of attaching the silyl compound 28 to the fiber is found in U.S. Pat. No. 3,652,761 ("the '761 patent") which is fully incorporated herein by reference, word for word and paragraph by paragraph. A second method for preparing the surface of fiber 12 and of attaching the silyl compound 28 to the fiber is found in U.S. Pat. No. 5,077,210 issued on Dec. 31, 1991 to Eigler et al and which is fully and completely incorporated herein by reference, paragraph by paragraph and word for word. Moreover, sensor assembly 10 of the preferred embodiment of the invention also includes a beam and/or light shaper 30 which in one embodiment comprises an optical fiber rod having an outside diameter of about 1 milli-meter and a length of about 6 centimeters, a focusing objective lens 32 having, in one embodiment, a focal length of about 30 milli-meters, a collecting/collimating lens assembly 36 having a collimating lens 37 and a collecting lens 39, notch filter 38 which in one embodiment comprises a commercially available "holographic super-notch filter" produced and sold by the Kaiser Optics Company, and lenses 40 and 42 which respectively comprise collimating and objective lenses; lens 40 having a focal length of about 30 milli-meters and lens 42 having a numerical aperture of about 0.55, in the preferred embodiment of the inventions In operation, light energy 15, which is generated by source 14, is communicated by lens 32 to shaper 30 which forms a diverging annular cone of light which is collimated by lens 40. The lens 40 collects light to form a thin annular cylinder of light which is communicated to the end of the optical fiber 12 outside of medium 20 as it passes through beamsplitter 18 and focusing objective lens 42. The shaped injected light propagates down fiber 12 at angles which are substantially equal to the critical angle with respect to the side surface of the fiber. As the light traverses down fiber 12, an evanescent field 43 is created in the vicinity of the fiber surface. Moreover, constituents 23 and 26 bind within the medium 20 and the created evanescent field cooperates with the tags 24 coupled to the bound constituents to create light energy 44 which is tunneled back through the optical fiber 12 and communicated by means of beamsplitter 18 and lens 42, through filter 38 after being collected by lens 39 and collimated by lens 37. It is then focused by lens 33 onto the detector 16. It will be understood by one of ordinary skill in the art that the holographic notch filter 38 substantially blocks all light at the incident wavelength of the source 14 while allowing substantially all fluorescent radiation to pass through lens 33 and be detected by detector 16. In this manner, only light energy from tags 24 is received by detector 16. With the exception of shaper 30 (and the surface treatment methodology of the invention), this general process is described in the '809 patent except that the holographic notch filter used in the apparatus of the preferred embodiment of the invention replaces the bandpass filter of the '809 patent so as to provide significantly improved signal reception sensitivity and signal to noise ratio signal reception characteristics. This improvement is accomplished because the holograplic notch filter 38 blocks and/or eliminates substantially all of the narrow laser line radiation while allowing broad band fluorescence radiation from the chemical tag (for example the fluorescence spectrum of Cy-5 has a half width of approximately 50 nm and full width of approximately 150 nm) to pass through it with minimal attenuation. In contrast, a conventional band pass filter with a bandwidth of about 10 nm would and is known by those of ordinary skill in the art, to substantially block the laser line radiation but would allow only a small fraction of the available fluorescence radiation to be collected and detected. While the biological immunoassay sensor assembly 10 of the preferred embodiment of the invention generally uses some of the principles found in the '809 patent and in other literature, it thus differs from these prior teachings in many aspects.

First, and without limitation, these prior and conventional biological fiber optic immunoassay sensors, such as those described in the '809 patent, use optical means for injecting light energy into the fiber, such as 12, which result in light energy propagating within the fiber over a broad distribution of angles ranging from zero degrees to the maximum cone angle with respect to the side surface of the fiber sensor (e.g. at angles encompassing the entire numerical aperture of the fiber sensor). Applicants have discovered that light energy injection over these wide angles is highly inefficient and provides less reliable measurement results than does the sensor of the preferred embodiment of the invention. That is, Applicants have noted that light energy entering the fiber and propagating at angles greater than the critical angle for total internal reflection will not be totally reflected at the fiber/liquid boundary and will be partially transmitted into the fluid surrounding the sensors, thereby failing to contribute to a uniform evanescent field along the sensor surface as well as stimulating bulk fluorescence in the fluid surrounding the sensor which drastically decreases instrument sensitivity and the signal to noise ratio.

Applicants have further noted that the strength of coupling of incident light energy to the evanescent field as a function of the light propagation angle at the sensor/fluid boundary is very strongly peaked and is strongest when the propagation angle is the critical angle for total internal reflectance. Consequently, optical means for injecting light into sensors which distribute the injected light across a wide range of angles, both couple inefficiently to an evanescent field and, because the light propagating at different angles impinges on different sections of the sensor walls, thereby generating evanescent fields which are not uniform and whose efficiency in stimulating and detecting fluorescence varies along the fiber.

That is, Applicants have noted that the received fluorescent signal varies or is a function of $Sin(°max)^8$ where $°max$ is the maximum angle of the cone of light being launched into the fiber. That is, to maximize overall biosensor sensitivity, it is desirable to have as much of the light as possible enter the optical fiber in a concentrated narrow range of angles which are close to or equivalent to the angle for total internal reflection or the "critical angle".

Applicants have discovered that injecting into fiber, light which propagates at or about the critical angle with respect to the side surface of the fiber, causes almost all of the injected light to totally internally reflect through out the length of the fiber, thereby providing an evanescent field which is generated about the entire surface of the fiber and which is further generated by almost all of the injected light, thereby having a higher strength and coupling efficiency than the fields generated by these prior and conventional biological sensors. Since the evanescent field is substantially uniformly generated around the entire surface of fiber 12 and is of relatively high strength, most of the tags 24 which are coupled to components 26 and which become attached to components 23 are activated by the field and detected and are "counted" or contribute to the measurements made or calculated by use of detector 16.

Applicants' invention has the further advantage of accomplishing this critical angle light injection without inserting a beam stopper or an annular aperture into the beam of light which enter into or is injected into the optical fiber and which functions to eliminate or prevent "non-critical angled light" from entering the fiber. More particularly, Applicants have found that such an aperture decreases the available light intensity for stimulating fluorescence and can reduce the ability of the biosensor assembly to collect fluorescent radiation which is emitted from the fiber face over a wide range of angles (from about 0° to about the angle corresponding to the maximum numerical aperture of biosensor assembly) after traversing through the optical fiber.

Figure 2:
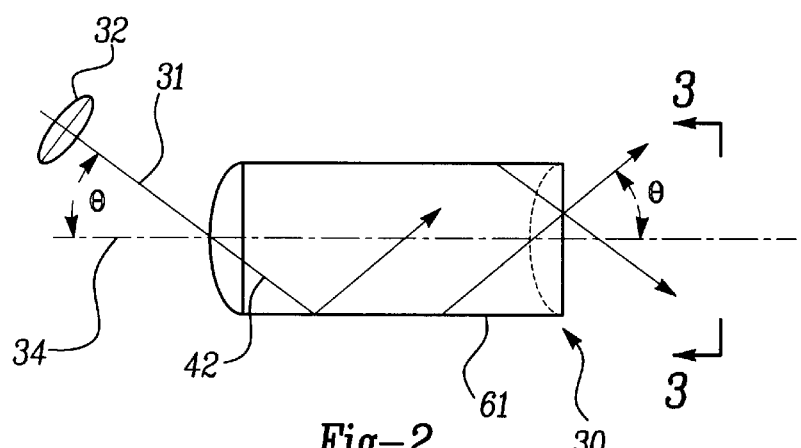
FIG. 2 is a schematic cross sectional view of the preferred embodiment of the light/beam shaping portion of the biological sensor generally shown in FIG. 1 and used in the various experiments delineated in this application.
Figure 3:
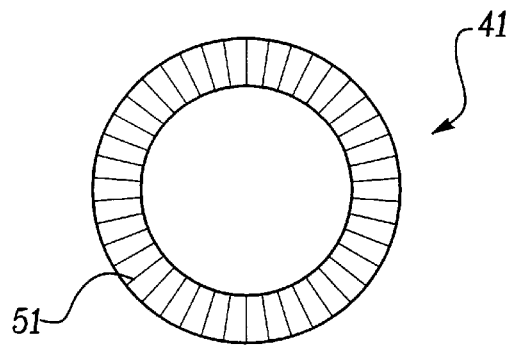
FIG. 3 is a schematic view of the shaped light emanating from the light/beam shaping portion of the biological sensor which is generally shown in FIG. 1 and which is more particularly shown in FIG. 2. More particularly, this shaped light is shown with respect to observations made in the direction of view line "3—3", shown in FIG. 2.

To gain a further understanding of the manner in which beam/light energy shaper 30 of the fiber optic biosensor of the preferred embodiment of the invention causes the light to be injected at this critical angle of fiber 12, reference is now made to FIGS. 2 and 3. The general purpose of this shaper is to inject an input beam of light having the energy concentrated within the interior of a narrow, cylindrical cone, and optically to perform a morphological inversion on the beam to produce an output beam shaped as a hollow annular cone with the light energy contained within a narrow annular region at the outside surface of the cone.

As shown in FIG. 2, lens 32, which in the preferred embodiment of the invention is of the type having a relatively long focal length (low numerical aperture) focuses the generated light rays (such as 31) into a cone having a half angle "φ" with respect to the longitudinal axis 34 of the light/beam shaper 30, which in the preferred embodiment of the invention, comprises a generally cylindrical solid optical fiber 31. The injected light propagates in skew rays down the fiber 31 which become uniformly azimuthly distributed within the fiber after propagating a sufficient length because of the initial spread of injection angles "φ". Upon exit, these rays exit from the fiber in a hollow annular cone 41 having a cone half angle of "φ" and an angular thickness set by the initial entrance of angle cone "φ". The spatial profile of the light output from the beam shaper as measured in a cross sectional plane normal to the axis of the output beam is shown in FIG. 3.

Figure 4:
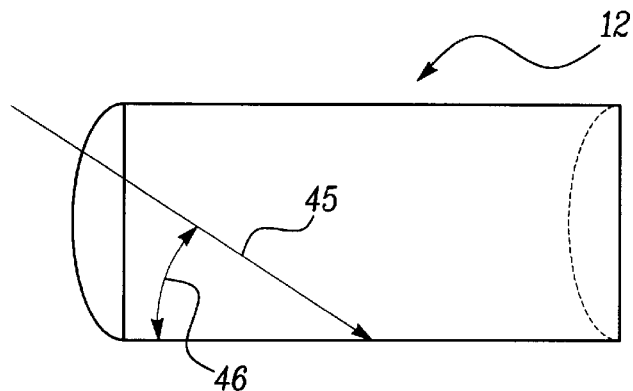
FIG. 4 is a schematic view of a representative light energy ray entering the optical fiber shown generally in FIG. 1 and being transmitted from the light/beam shaping portion shown best in FIG. 2.
Figure 8:
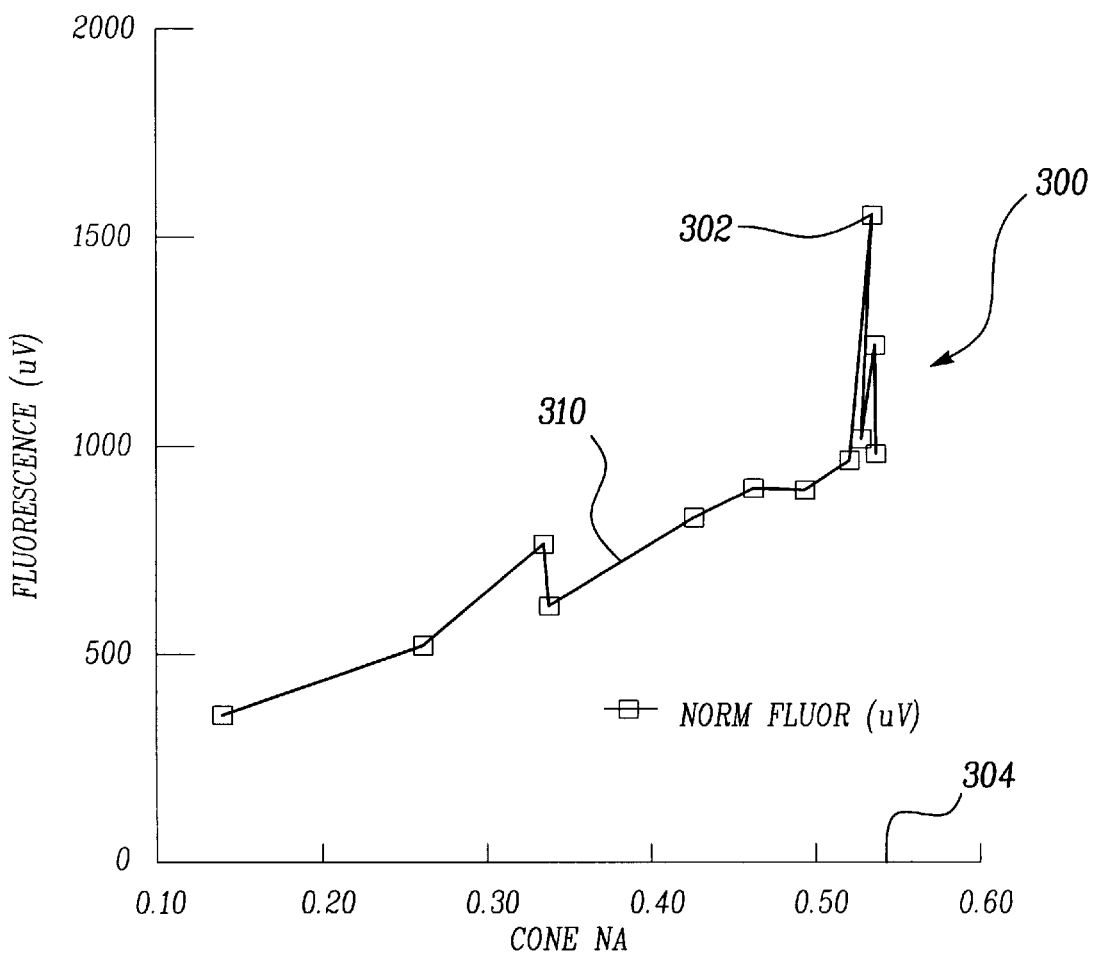
FIG. 8 is a graph demonstrating measurements made of fluorescence versus numerical aperture for the immunoassay biological sensor shown and described in FIG. 1

Applicants have found that this beam shaped light profile can be used to inject light into a fiber optic biosensor in such a way that substantially all injected light is propagating at the same angle. Furthermore, by appropriate choice of relay and focusing optics, substantially all injected light can be made to propagate at the critical angle. For example, in FIG. 1, a collimating lens 40 is used to convert the annular cone emerging from the beam shaper 30 into an annular cylinder which passes through the beamsplitter 18 and is focused into the fiber 12 using a microscope objective lens 42. By selecting the focal length of lens 40, the diameter 51 of the annular cylinder of light entering the lens 42 may be adjusted to cause the injected and shaped light energy 45 to enter and propagate at the critical angle 46 in the fiber 12 as shown in FIG. 4, thereby achieving greater accuracy and sensitivity than was previously available. The benefits of such "critical angle" light injection are shown in graph 300 of FIG. 8 which represents data measurements obtained by use of the assembly depicted in FIG. 1. Such data represents a plot of fluorescence versus cone angle of the injected light. As shown, peak or maximum fluorescence occurs at portion 302 of the graph, corresponding to the critical angle 304 of the fiber 12. More particularly, in this experiment, a fiber having fluorescence bound to its surface was inserted into a sensor cell. The laser was mounted so that the cone angle at which light was injected into the fiber sensor was varied and the fluorescence response of the sensor was measured. As shown in by graph line 310, by concentrating the rays at the critical angle, the sensitivity of the immunoassay biological sensor is greatly and dramatically increased. More particularly, this is shown by peak 302, representing a dramatic increase in detected and/or received fluorescence at light injection angles very close or equal to the critical angle.

Secondly, and without limitation, the biological immunoassay sensor 10 of the preferred embodiment of the invention also differs from that found in prior literature, including the '809 patent and the '761 patent, by use of a fiber optic surface treatment methodology to reduce and/or eliminate the binding of proteins and other undesirable components to component 23, which under previous embodiments resulted in errant measurements and/or calculations. More specifically, the non-specific binding surface treatment methodology of the preferred embodiment of the invention is set forth in the following experiments conducted by Applicants and denoted in this Application as "Examples". It should again be noted that the surface treatment and light injection methodologies are independent and could be mutually exclusive in their respective application and use.

EXAMPLE I

Demonstration of Nonspecific Binding Protection

About one hundred and twenty (120) meters of optical fiber was obtained from the 3M Specialty Optical Fibers Division of the 3M company which is located at 420 Frontage Road, West Haven Conn. 06516. More particularly, this commercially obtained optical fiber comprises part number FT-400-umt, has an identification number of 200713-3546, has an attenuation of 4.8 dB/km @ 812 nm, a bandwidth of 13 MHz, a numerical aperture of 0.39 with a measured deviation of =/−0.02, a core diameter of 400 um with a measured deviation of +/−8 um, a clad diameter of 430 um with a measured deviation of +5 to −15 um, a buffer diameter of 730 um with a measured deviation of +/−30 um, and a proof level of 50 KPSI. From this fiber roll, two substantially similar fiber segments were cut by a cutting technique known to those of ordinary skill in the art. The length of these two substantially similar fiber segments was about three inches. Both fiber segments were stripped of cladding by rubbing with an acetone soaked kimwipe and immersed, at room temperature, into commercially available and conventional concentrated nitric acid, although any other method or technique known to those of ordinary skill in the art and sufficient to produce and "ultraclean glass surface" may be used, such is glass discharge cleaning.

After the immersion, fibers were rinsed with doubly distilled deionized water and one fiber was not treated further. The other fiber segment was air dried for about five to about ten minutes at a temperature of about seventy to about seventy-five degrees Fahrenheit. The treated fiber segment was then dipped and immersed for about one second into a test tube substantially filled with a chemical from the family of amorphous fluoropolymers and, more particularly, Teflon AF® produced and commercially available from the Specialty Polymers Division of the DuPont Company, located at P.O. Box 80713, Wilmington, Del. 19880-0713. After the dipping, the treated fiber segment was air dried for about five to about ten minutes at a temperature of about twenty-five to about fifty degrees Centigrade. After the air drying was completed, the first fiber segment was baked at a temperature of about one hundred and sixty five degrees Centigrade for about five minutes and then further baked at a temperature of about three hundred and thirty degrees Centigrade for about ten to about fifteen minutes. After the second baking step was completed, the first fiber segment was substantially and fully immersed into a test tube of Fluorinert FC-75™, obtained from the Specialty Polymers Division of the DuPont Company for about thirty to about forty-five minutes. The fiber was then rinsed for about 15 seconds in a second tube of Fluorinert FC-75™ and allowed to air dry. The foregoing surface treatment methodology applied to the treated fiber segment comprises the non-specific binding surface treatment methodology of the preferred embodiment of the invention. In a second preferred embodiment, a segment of fiber which has been commercially produced to be clad with Teflon-AF (e.g. Polymicro FSU) was substantially and fully immersed into a test tube of Fluorinert FC-75™ as previously described. The other fiber segment was not treated in any manner whatsoever in order to assess the operation of a first biological immunoassay sensor utilizing the treated optical fiber segment, relative to the operation of a second biological sensor utilizing the conventional or "untreated" optical fiber segment.

Figure 6:
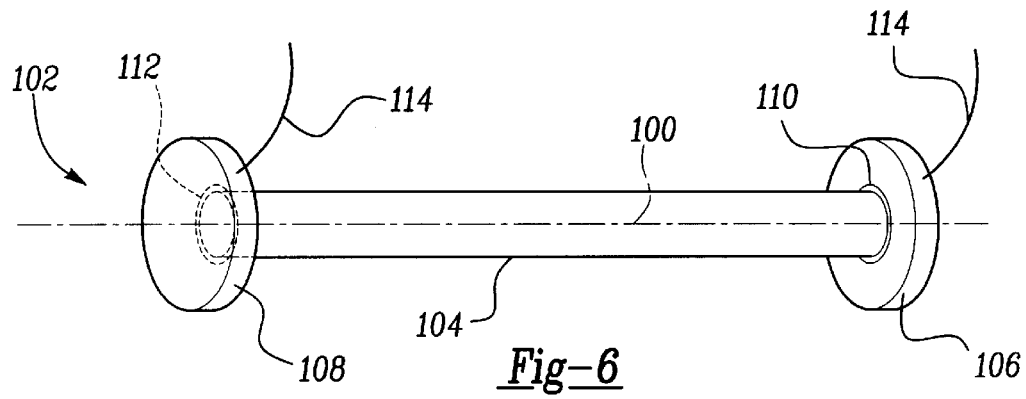
FIG. 6 is a perspective view of one representative capillary flow cell used in the Examples which are described in the application.

Two fiber optic immunoassay sensors were created and were substantially similar to that shown in FIG. 6. The fibers 100, each having a diameter of about 400 um with about a 20 um TEFLON AF® cladding on the ends were centered in individual capillary flow cells, in a manner that prevented them from touching the walls. More particularly, one such fiber-flow cell assembly is shown in FIG. 6. The same discussion applies equally to the remaining flow cells. Fiber 100 was centered within flow cell tube 104 by placement within opposing derin disks 106, 108. Imbedded Viton O-rings 110 and 112 were used to securely fit tube 104 onto respective disks 106 and 108, thereby ensuring that no leakage of fluid occurred in the vicinity of the disk-tube interface. Teflon flow tube 114 was used to fill tube 104. The volume of the capillary flow cells was approximately 80 micro-liters. More particularly, the first such biological immunoassay sensor used the treated fiber segment as fiber 100 while the second biological immunoassay sensor used the "untreated" fiber segment as fiber 100. Both sensors, and the concomitant light generation and detection assemblies were substantially equivalent to that shown and described with respect to FIG. 1. Moreover, both sensors utilized the beam/light shaper shown and described with respect to FIG. 2.

Next, a solution containing Bovine Serum Albumin (BSA) was made to flow into both fiber optic immunoassay sensors. This is the conventionally used method to reduce nonspecific or "undesirable" binding upon the solid surfaces. More particularly, the BSA was prepared by placing about one percent by weight of BSA into a beaker containing a phosphate buffer having a pH of about 7.2 and representing about a 0.1 Molar concentration. Both fiber segments were immersed into the BSA concentration for about thirty minutes. Anti-estrone-3-glucuronide monoclonal, tagged with fluorophore Cy-5 had previously been prepared as described below.

Particularly, a five pack of Fluorolink™ Cy5 Reactive Dye was obtained from Biological Detection Systems, Inc., located at 955 William Pitt Way, Pittsburgh, Pa., 1 5238. One of these packs was mixed with a concentration of about one milligram per one milliliter of mouse antibody monoclonal to Estrone-3-glucuronide ("anti-E1-g") and sodium carbonate buffer having a pH of about 9.3 and a concentration of about 0.1 Molar. The combination was placed in a stationary position for about forty-five minutes at a temperature of about seventy-two degrees Fahrenheit. The combination was placed into a conventional and commercially availed Centricon 30 concentrator to reduce the volume to about 150 microliters and was centrifuged at about a speed of 5550 revolutions per minute for about twenty minutes. While the centrifugation was continuing, a commercially available Sephadex G-50 column was prepared for chromatography.

After the centrifugation was completed, a 150 microliter sample was applied to the column by techniques known to those of ordinary skill in the art and eluted with about 0.1 molar concentration of phosphate buffer having a pH of about 7.2. The peaks emerging from the column were detected by their absorbance at 280 nm. The first peak was collected into a test tube, mixed and placed in a cuvette and inserted into a spectrophotometer. Sample absorption at 280 and 650 nanometers was observed. More specifically, the concentration of antibody was calculated from equation 1 and the ratio of Cy-5 per antibody was calculated from equation 2.

$$\text{Equation 1:} \quad \text{Antibody concentration} = \frac{A_{280} - .05(A_{650})}{170,000}$$

Equation 2: Cy5 concentration=$A_{650}/200,000$

Ratio: Cy5 concentration/antibody concentration

Sufficient Cy-5 tagged antibody was added to 0.1M phosphate buffer, pH 7.2 containing 0.1% BSA to yield a concentration of about $10^{-7}$M antibody Cy5. This solution was made to flow into both sensors and the fluorescence resulting from binding of the antibody to the fiber was measured using the previously described sensor apparatus.

Figure 5:
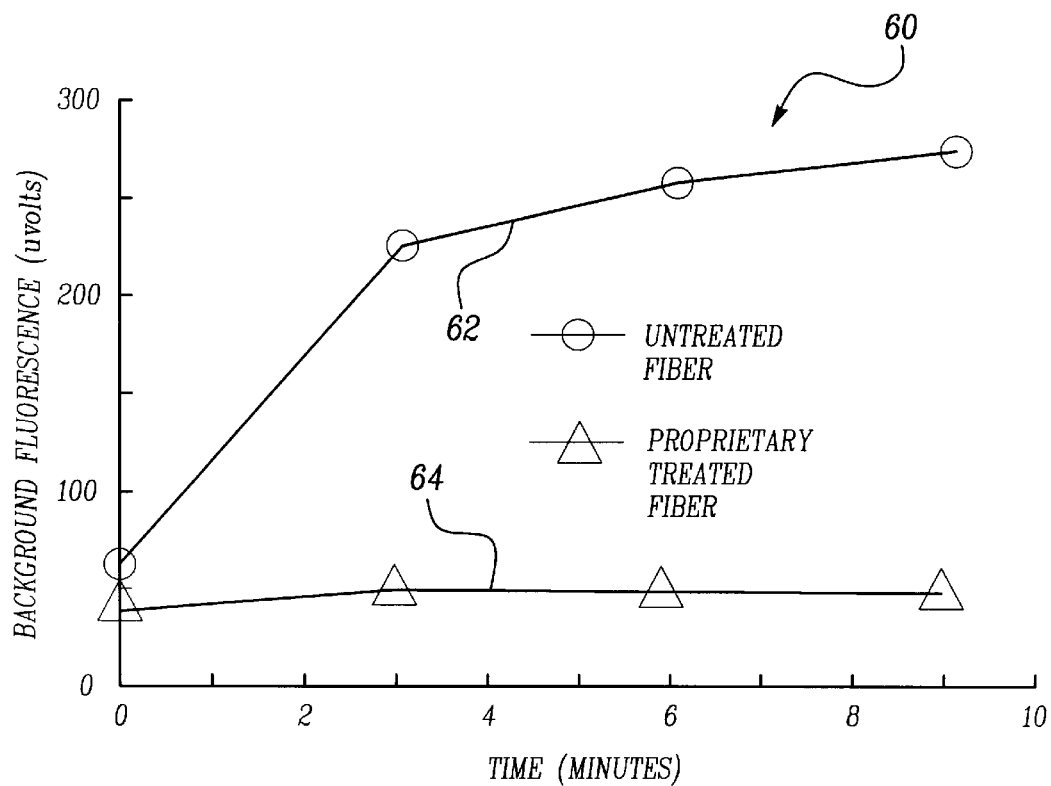
FIG. 5 is a graph of time versus background fluorescence resulting from measurements made in accordance with Experiment 1 and further illustrating the usefulness of the non-specific binding surface treatment methodology of the invention.

Since no antigen to the antibody was present on either sensor surface, any observed or detected fluorescence "tunneling" must necessarily be caused by non-specific "undesirable" binding of the fluorophore labeled antibody to the sensor surface. As shown in Graph 60 of FIG. 5, the "untreated" sensor or fiber (graph line 62) showed a great increase in detected fluorescence tunneling while the treated sensor (graph line 64) did not. The inescapable conclusion to be drawn is that the surface treatment methodology set forth above reduces and/or virtually eliminates "undesirable" and/or non-specific binding of antibody on the surface of the fiber.

EXAMPLE II

Demonstration of the Requirement for each Procedural Step in Achieving Nonspecific Binding Protection 400 micron fused silica fibers as described in the following table were mounted in the previously described flow cells. The cells were filled with Fluorinert FC-75® and left at room temperature (about seventy degrees Fahrenheit) for about thirty minutes. After this period of time, about two milli-liters of Fluorinert FC-75® was pumped rapidly through the capillary flow cells. Fluorinert FC-75® solvent was next removed by injection of about two milliliters of isopropanol followed by about two milliliters of distilled water. Then, the capillary tubes were filled with a buffer solution containing horseradish peroxidase (HRP) from the Sigma Company and having a product number of P8375. These fibers were removed from the flow cells, and, along with a commercially available TEFLON® clad 400 micron fused silica fiber which had not been treated with Fluorinert FC-75®, were inserted into separate HRP filled capillary tubes. After about one hour, the fibers were thoroughly rinsed with distilled water for about ten minutes each and placed in capillaries containing ELISA substrate 3,3',5,5'-tetramethylbenizidine, obtained from the Chemicon Company located at 28835 Single Oak Drive. Temecula, Calif. 92590. Observations were made for the development of a blue or "bluish" color. The experiment results are summarized and shown in table 1 below:

| | Fiber Type | Baked | Fluorinert Treatment | Effect on HRP substrate |
|---|---|---|---|---|
| 1) | Unclad 3M fibers without TEFLON ® | yes | yes | turned substrate blue |
| 2) | Commercial TEFLON ® clad fibers | yes | no | turned substrate blue |
| 3) | Unclad 3M, TEFLON ® dip-coated fibers | no | yes | turned substrate blue |
| 4) | Commercial TEFLON ® clad fibers | yes | yes | substrate unchanged |
| 5) | TEFLON AF ® dip-coated fibers | yes | yes | substrate unchanged |

The above summarized data indicates that there exist or appear to presently exist three distinct processes or methodology steps that are required to endow the fused silica fibers with a surface that does not display non-specific attraction toward proteins: (A) Fibers must be coated with a mixture of amorphous fluoropolymers such as TEFLON AF®. (B) Fibers must be baked; and, (C) Some portions of the TEFLON AF® must be removed such as was accomplished by immersion in Fluorinert FC-75.

EXPERIMENT III

Demonstration that the Nonspecific Binding Protection does not Impair the Ability of the Fiber to React with Silanes Because fibers are made "sensitive" to the substance which they will measure by the coupling of biologically active molecules to the fiber surface via silane chemistry, it is important that the process by which non-specific binding protection is obtained does not prevent the fibers from reacting with silanes. In order to test that this attribute was present in fibers which were treated by the non-specific binding methodology of the preferred embodiment of the invention, fibers which had received non-specific binding protection and fibers which had not received this protection were both coupled to Cy-5 horseradish peroxidase via a silane according to the method of Bhatia which is fully set forth in the article entitled "Use of Thiol-Terminal Silanes and Hetero Bifunctional Crosslinkes for Immobilization of Antibodies on Silica Surfaces", appearing in *Analytical Biochemistry*, 178, 408–413 (1989), and which is fully incorporated into this application by reference, paragraph by paragraph and word for word.

Both types of fibers were tested for HRP activity as before. Both immediately turned the substrate a smooth blue. This is distinguished from the blue color seen in the previous experiment by the observation that the blue color in the previous portion of this experiment was uneven, having darker and lighter regions visible within the capillary. The blue color in this portion of this experiment was completely even in distribution, indicating a controlled silanized surface rather than a random non-specifically bound surface. The blue color also developed more rapidly in this portion of the Experiment 2. Fluorescence of a type 1 and a type 2 fiber was measured using the assembly shown and described with reference to FIGS. 1–3, Innovation Associates fiber optic fluorimeter. The type 1 fiber registered a fluorescence of 3.36 uvolts. The type 2 fiber registered 3.26 uvolts, not a significant difference between the two. Thus, it is clear that the surface treatment methodology of this invention does not interfere with silanization.

These results were extended by using commercially available single crystal slices of silicon wafers adapted for use in electronic circuits. Both wafers were cleaned. One wafer was coated with Teflon-AF and it was baked onto the silicon wafer using the above heat treatment cycle set forth in Experiment I. The second wafer was uncoated. The Teflon AF coating on the treated wafer was then removed using Fluorinert FC-75. Both silicon wafers were then incubated with HRP for an hour. After being thoroughly rinsed with commercially available and conventional distilled water, the wafers were placed in conventional beakers and 1 ml of ELISA substrate 3,3',5,5'-tetramethylbenzidine was rolled down the wafers into the beakers and observed for development of a blue color. The solution around the untreated silicon wafer immediately turned an intense shade of blue, whereas the solution around the wafer treated by baking on the Teflon-AF and then removing it, showed little or no color change. Hence, the surface treatment methodology of the preferred embodiment of the invention prevented non-specific binding to occur on one treated wafer.

In summary, the above-referenced experiments conclusively show that Applicants' surface treatment methodology reduces and/or eliminates non-specific binding and does not adversely affect the ability of silane molecules from coupling to or connecting/adhering to the fiber surface. The treatment is applicable to diverse silicon-based surfaces including at least glass fibers and silicon wafers.

The numerical aperture (NA) of an unclad fiber immersed in the measurement fluid is larger than the NA for an unclad fiber in air or a fiber with its cladding intact. For evanescent wave biosensors, it is necessary to launch light into the fiber with the cone angle corresponding to the NA of the fiber when immersed in the fluid being used as the test medium (typically water). If the fiber were completely immersed in the fluid this would present no problem. However, in order to hold (support) the fiber, the fiber ends must be held by some other solid material and this results in a large loss of both input and return light signals. For example, if the fiber end lies outside of the fluid, any light entering the fiber with a cone angle exceeding the NA of the unclad fiber will hit the fiber glass/air interface with an angle greater than the critical angle for the glass/air interface and will exit the fiber. Similar losses will occur if an attempt is made to launch the beam into a clad fiber or a fiber supported by conventional dielectric materials (plastic, resins, etc.). Losses also occur in the returning fluorescent signal as the higher order modes are stripped by the NA change occurring where the signal enters the portion of the fiber touching the support material. Thus a method is needed for allowing light from a high NA optical illumination system to be launched into an unclad fiber and to allow a fiber to be held (supported at one or both ends) by a structure without causing losses in the input or return signal.

Figure 7:
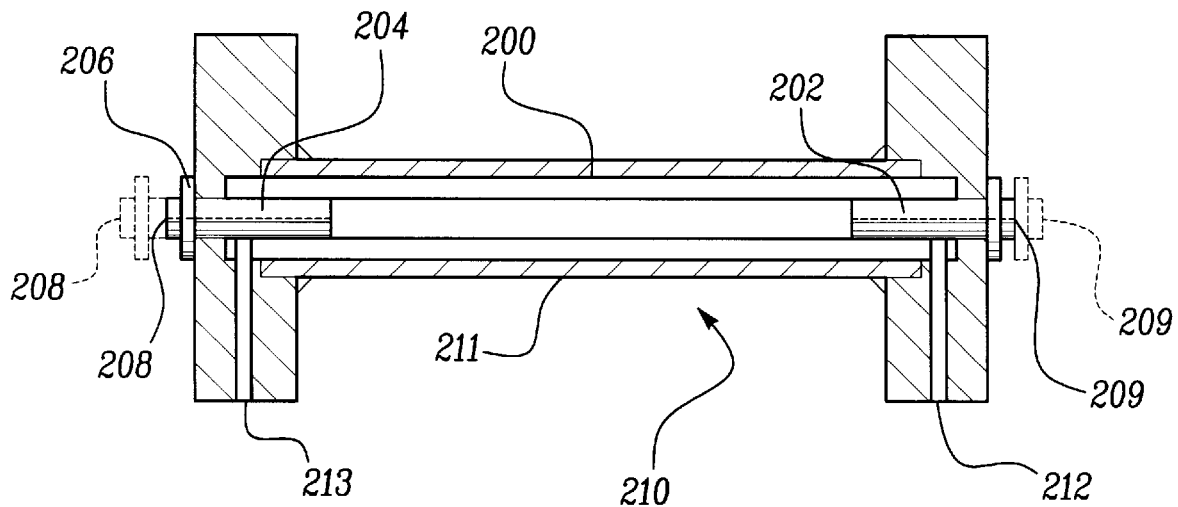
FIG. 7 is a side views of an exemplary immunochemical biological sensor assembly employing the fiber treatment/placement methodology of the invention and having improved light energy loss characteristics over that of the prior art.

Referring now to FIG. 7, there is shown a optical fiber 200 having improved light input and output loss characteristics over the other prior art and which may be used to replace fiber 12 in the assembly shown and described with respect to FIG. 1. It should be noted by one of ordinary skill in the art that the following biological fiber placement methodology may be used in combination with or be independent from the methodologies and apparatuses described earlier in this application.

Specifically, as shown in FIG. 7, optical fiber 200 has a TEFLON® coating 202, 204 which is applied at each of the ends of the fiber. The coating is not applied to the input and output face of the fiber but rather it is applied, according to the teachings of the preferred embodiment of this invention, to the longitudinal portion of the end of each fiber 200. Since the coating has an index of about 1.3 (close of that of water) most of the light which would be totally internally reflected at the glass/water interface is also totally internally reflected at the glass/Teflon-AF boundary. Moreover, the sample cell 210 allows or places the fiber 200 into the medium of interest.

More particularly, the fiber 200 is usually precoated with Teflon-AF®. According to the methodology of the preferred embodiment of the invention, an appropriate solvent, such as Fluorinert®, is used to strip or take away the Teflon-AF® from both opposed ends of the fiber 202. Once removed, the strip ends are recoated with Teflon-AF® thus producing a fiber with a bare and clean middle region which may be chemically sensitized; a fiber with coated ends which may be used in handling and mounting the fiber without damaging the chemically sensitive surface; and, a fiber with coated ends which may be easily sealed, such as by means, of glue, epoxy, liquid sealants, or gaskets (such as by means of seal 206) into the end caps 208, 209 of the assembly 210 to provide a relatively leak-tight flow tube 211 around the fiber sensor without inducing severe optical losses. Fluids are flowed through the flow ports 212 and 213.

The fiber, as shown best in FIG. 7, may be held or supported by the sample cell only at the Teflon® treated ends, without causing losses in input or received light signal by using structures which clamp around or attach the Teflon® coated areas of the fiber.

It is to be understood that other changes and modifications may be made to the above-described apparatuses and methodologies without departing from the scope and/or spirit of the various inventions. It is intended that all matters included and/or contained in the above description or shown in the accompanying drawings shall be or shown in the accompanying drawings shall be interpreted in an illustrative and teaching lens but not a limiting sense. That is, the light injection, non-specific binding surface treatment methodology and mounting treatment methodology all have utility beyond their use in the biological immunoassay sensor described and claimed in this Application. For example, and without limitation, the surface treatment methodology may find use in the production of biological field effect transistors.

We claim:

1. A method to treat a surface in order to substantially reduce binding of certain constituents to said surface, said method comprising the steps of:

applying a chemical from the group consisting of amorphous copolymers of perfluoro (2,2 dimethyl-1,3 dioxole) and tetrafluoroethylene to said surface;

baking said surface for a predetermined period of time and at a predetermined temperature; and partially removing said applied chemical from said surfaces by immersing said surface into a second chemical from the group consisting of perfluorochemical inert liquids and removing said second chemical from said surface after a predetermined period of time.

2. The method of claim 1 wherein said step of predetermined period of time comprises about ten minutes.

* * * * *

UNITED STATES PATENT AND TRADEMARK OFFICE
CERTIFICATE OF CORRECTION

PATENT NO. : 5,952,035
DATED : September 14, 1999
INVENTOR(S) : Erb et al.

It is certified that error appears in the above-identified patent and that said Letters Patent is hereby corrected as shown below:

<u>Column 1,</u>
Line 5, -- This invention was made with government support under grants HD29654 and ES06629 awarded by the National Institute of Health. The government has certain rights to the invention. --

Signed and Sealed this

Thirtieth Day of October, 2001

*Attest:*

*Nicholas P. Godici*

NICHOLAS P. GODICI
*Attesting Officer*  *Acting Director of the United States Patent and Trademark Office*